United States Patent [19]
Knapp et al.

[11] Patent Number: 5,716,407
[45] Date of Patent: Feb. 10, 1998

[54] METHOD OF RENDERING IDENTIFIABLE A LIVING TISSUE IMPLANT USING AN ELECTRICAL TRANSPONDER MARKER

[75] Inventors: Terry R. Knapp, Neuchatel, Switzerland; John Steuart, Berkeley, Calif.

[73] Assignee: Lipomatrix, Incorporated, Neuchatel, Switzerland

[21] Appl. No.: 375,815

[22] Filed: Jan. 20, 1995

Related U.S. Application Data

[63] Continuation-in-part of Ser. No. 221,706, Apr. 1, 1994, Pat. No. 5,674,288, which is a continuation-in-part of Ser. No. 934,785, Aug. 24, 1992, Pat. No. 5,300,120.

[51] Int. Cl.$^6$ ............................ A61F 2/02; A61F 2/12
[52] U.S. Cl. ........................................ 623/11; 623/8
[58] Field of Search ........................... 623/7, 8, 11, 66; 340/573, 825.54, 825.55, 825.69, 825.72, 825.34

[56] References Cited

U.S. PATENT DOCUMENTS

| | | |
|---|---|---|
| 3,839,708 | 10/1974 | Bredesen et al. . |
| 3,949,388 | 4/1976 | Fuller . |
| 4,262,632 | 4/1981 | Hanton et al. . |
| 4,361,153 | 11/1982 | Slocum et al. . |
| 4,399,821 | 8/1983 | Bowers . |
| 4,531,526 | 7/1985 | Genest . |
| 4,618,861 | 10/1986 | Gettens et al. . |
| 4,703,756 | 11/1987 | Gough et al. . |
| 4,730,188 | 3/1988 | Miheiser . |
| 4,746,830 | 5/1988 | Holland . |
| 4,854,328 | 8/1989 | Pollack . |
| 4,863,470 | 9/1989 | Carter . |
| 4,875,483 | 10/1989 | Vollmann . |
| 4,992,794 | 2/1991 | Brouwers . |
| 5,010,893 | 4/1991 | Sholder . |
| 5,012,286 | 4/1991 | Kawano et al. . |
| 5,028,918 | 7/1991 | Giles et al. . |
| 5,036,869 | 8/1991 | Inahara . |
| 5,041,826 | 8/1991 | Milheiser . |
| 5,084,699 | 1/1992 | DeMichele . |
| 5,095,309 | 3/1992 | Troyk et al. . |
| 5,211,129 | 5/1993 | Taylor et al. . |
| 5,218,343 | 6/1993 | Stobbe et al. . |
| 5,235,326 | 8/1993 | Beigel et al. . |
| 5,300,120 | 4/1994 | Knapp et al. . |
| 5,545,221 | 8/1996 | Hang-Fu ................. 623/8 |

FOREIGN PATENT DOCUMENTS

| | | |
|---|---|---|
| 0619 101 A1 | 12/1994 | European Pat. Off. . |
| WO8704900 | 8/1987 | WIPO . |
| WO9207505 | 5/1992 | WIPO . |

*Primary Examiner*—Debra S. Brittingham
*Attorney, Agent, or Firm*—Howell & Haferkamp, L.C.

[57] ABSTRACT

A passive transponder may be encoded with a number or code of up to 64 binary bits and then associated with or mounted to virtually any living tissue implant for implantation in a human. After implantation, the transponder's code may be conveniently read with a hand held electromagnetic reader which may merely be brought within proximity of the transponder. The encoded transponder may thus be read in a non-invasive procedure and without the use of any sophisticated or potentially harmful medical equipment or technology such as X-ray. The information encoded in the transponder may correspond to patient demographics and implant data to aid in tracking the implant's progress and use for medical as well as legal reasons.

11 Claims, 5 Drawing Sheets

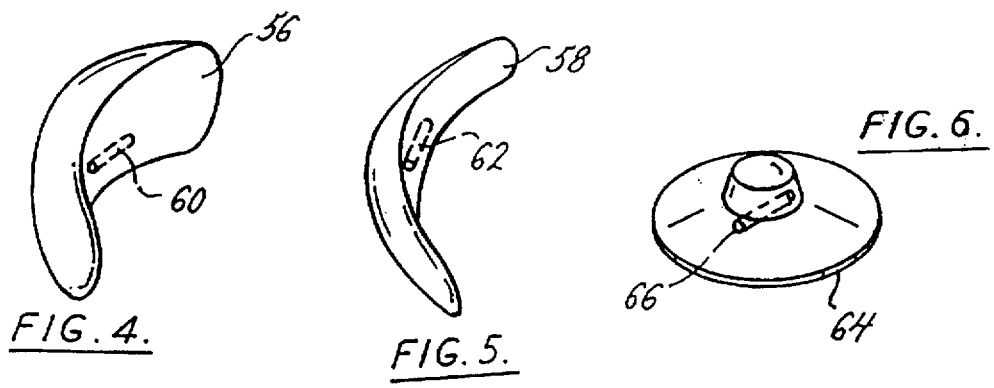
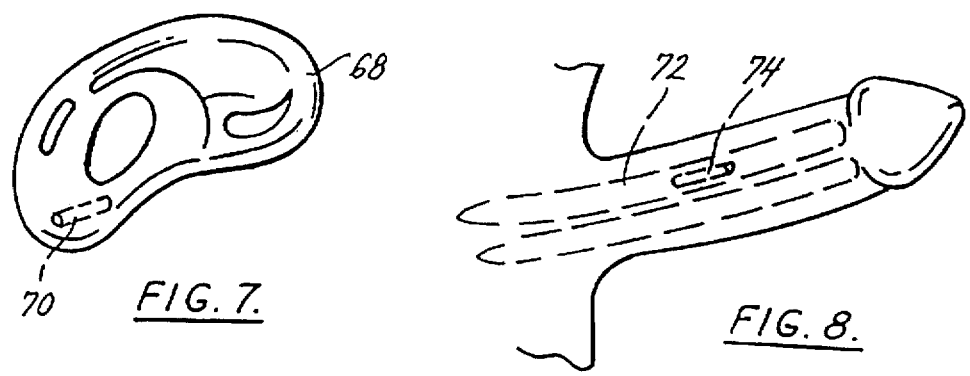
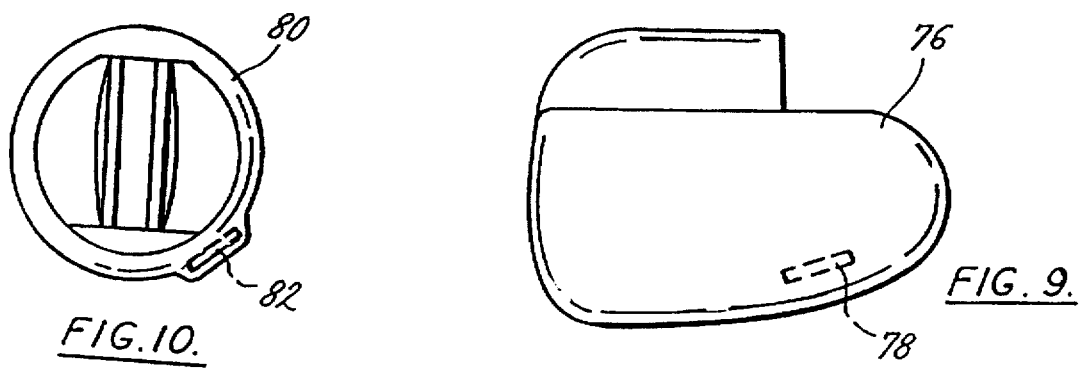

METHOD OF RENDERING IDENTIFIABLE A LIVING TISSUE IMPLANT USING AN ELECTRICAL TRANSPONDER MARKER

CROSS-REFERENCE TO RELATED APPLICATION

This application is a continuation-in-part of Ser. No. 08/221,706, filed Apr. 1, 1994, now U.S. Pat. No. 5,674,288, Oct. 7, 1997, which is a continuation of Ser. No. 934,785, filed Aug. 24, 1992, now U.S. Pat. No. 5,300,120.

BACKGROUND AND SUMMARY OF THE INVENTION

With the advance of medical technology, there are a number of medical prostheses and devices which are implantable in humans for re-constructive and/or cosmetic purposes. These include breast implants; penile implants; musculature and other soft tissue implants; pace makers; valves; artificial joints and limbs such as knees, shoulders, legs, fingers, etc.; pins; screws; plates; rods; nails and other braces and supports. In order to ensure the continued safety and health of patients receiving these implants, the Safe Medical Device Act of 1990 has been enacted which dictates that manufacturers of Class III implantable medical devices institute a device registry for tracking of their devices, notification of patients, and otherwise monitoring these implants after they have been placed in a patient. Compliance with this Act has been proposed through a method of tracking which requires the surgeon who implants the device to complete and return a form or card with patient demographic data and implant data to the manufacturer or to a third party registry service. This method requires careful accumulation of data by a surgeon or his staff as well as secure inventory control procedures in order to ensure that the data is properly associated with the correct implant. Additionally, there is a risk of loss of data entirely resulting from misdirected or lost communications. Furthermore, access to this data can be impeded in the event of an emergency situation or other circumstances which interfere with a patient's ability to recall or report the proper information which medical personnel may then use to access the registry and data contained therein.

The issues described above with respect to medical prostheses and devices are very similar for living tissue transplants or implants, including complete organs. As with implanted medical prostheses and devices, transplanted tissue is subject to rejection, infection, and a host of other medical complications. Just as pace maker implant patients are closely followed and reviewed by the health care system, so are burn victims with skin grafts, lung transplant patients, kidney transplant patients, etc. For these patients, the ready availability of information relating to the transplanted tissue and the medical procedure utilized would be very helpful not only in treating the patient but also in tracking and monitoring the patient's progress. In emergency situations, access to this data may well be critical to proper diagnosis and treatment, especially if a disorder relating to the transplanted living tissue is what causes the medical emergency.

There have been some suggestions in the prior art of marking the implants themselves with, for example, a radiopaque marker or other marker which contains the information relating to the implant. Ideally, this data could then be viewable by X-ray or some other non-invasive manner. However, there are difficulties with these prior art approaches. First of all, a breast implant with a radiopaque marker would at least partially obscure or mask tissue which is desired to be viewed in order to detect artifacts relating to tumors or the like for diagnosing cancer. Obviously, this is highly undesirable as the incidence of breast cancer presents a significant risk to many females. Additionally, repeated exposure to X-ray is not generally considered healthful or desirable and represents at least an added inconvenience entailing some degree of expense to recall or access the implant data. Therefore, radiopaque markers have not been viewed as a suitable long-term solution to this problem.

In order to solve these and other problems in the prior art, and in order to provide a convenient, fool proof marker secured to the implant itself and yet readable in a non-invasive manner, the inventors herein have succeeded in designing and developing an implant which incorporates a passive transponder which may be encoded and subsequently accessed with a hand held electromagnetic reader in a quick and inexpensive procedure. The passive transponder may be secured to the implant by any convenient means. For example, in a breast implant, the multi-layered shell for the implant may be laminated around the transponder to thereby be permanently and securely fixed to the implant. The transponder may be laminated in the sidewall of the shell, or between layers which comprise the seal patch which is applied to the shell to seal the mandrel opening. Similarly, the transponder may be laminated onto the surface of most other implants in an unobtrusive location. In some other implants, the transponder may be inserted into a hole or inlay and sealed in place.

As with non-living medical devices and prostheses, a transponder may be associated with a living tissue implant and even implanted at the same time as the medical procedure used for implanting the living tissue. Depending on the particular living tissue being implanted, the transponder may or may not be incorporated directly into the transplanted organ or tissue and instead may be separately implanted. This decision would best be left to the medical professional or surgeon performing the medical procedure on a case by case basis, although recommendations could be provided in order to ensure a degree of standardization. The transponder could be encoded with data relating to the living tissue and would be permanently and securely implanted in the patient to provide ready access to data relating to the living tissue implant.

As passive transponders are commercially available in a cylindrical shape sized at 2 mm in diameter and 11 mm in length, the patient will not sense any discomfort or even the presence of the transponder. Also, the transponder may be encoded with any suitable encoding scheme. A commercially available transponder presently provides for the storage of up to 64 binary bits of data. This data capacity may accommodate the direct storage of much, if not all, of the information desired to be recorded and maintained in a device registry. Furthermore, the storage capacity of the transponder is expected to be increased as further development occurs over time. Alternately, a number, collection of numbers, combination of numbers and letters, or other indirect code may be stored which after reading may be used to access a data bank which itself contains the desired information. Of course, if information is directly stored in the implant, it becomes immediately available upon reading the transponder. This provides ready access to information in emergency situations. Alternately, with the widespread availability, accessibility, and use of computers over telecommunications networks including telephone lines, it is not generally considered to be unduly limiting to provide that the code read from the transponder be then used to access an appropriate data bank in order to obtain the patient demographics, manufacturer's name, date of manufacture, surgeon's name, date of implantation, etc.

A companion hand held electromagnetic reader is also commercially available which emits a low frequency magnetic field to activate the passive transponder and thereby cause it to transmit its encoded data to the reader. With this particular commercial device, no battery or other source of electrical power need be included in the passive transponder. This further reduces the size required for the transponder and renders it particularly suitable to this application.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 4 is a perspective view of a soft chin implant with passive transponder mounted therein;

FIG. 5 is a perspective view of a rigid chin implant with a passive transponder mounted therein;

FIG. 6 is a perspective view of a nipple transplant with a passive transponder mounted therein;

FIG. 7 is a perspective view of an otoplasty implant with a passive transponder mounted therein;

FIG. 8 is a perspective view of a penile implant, surgically implanted, with a passive transponder mounted therein;

FIG. 9 is a top view of a pace maker with a passive transponder mounted thereon;

FIG. 10 is a top view of a heart valve with a passive transponder mounted to the edge thereof;

DETAILED DESCRIPTION OF THE PREFERRED EMBODIMENT

Figure 1:
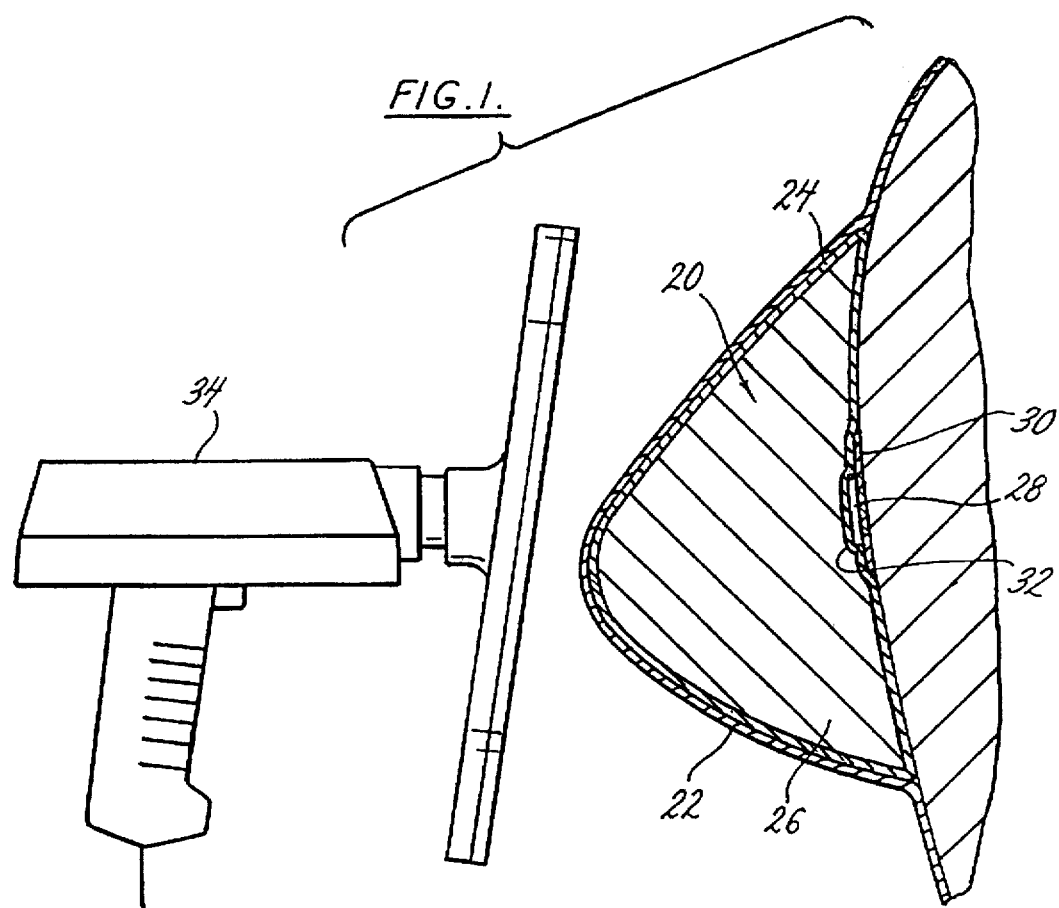
FIG. 1 is a perspective view of a breast implant containing a passive transponder with a hand held reader in position to read the encoded data contained therein.

As shown in FIG. 1, a breast implant 20 has been implanted in a female's breast 22 and includes a silicone shell 24 inflated with an appropriate fill material 26. At the posterior side of the implant 20 is shown the transponder 28 which has been laminated between adjacent layers 30, 32 of the shell 24. Transponder 28 may be any passive transponder such as a Trovan Model ID100 available from Electronic Identification Systems Ltd. of Santa Barabara, Calif. This particular transponder is designed to be environmentally independent and suitable for operation while being directly submerged in liquids. Furthermore, it may be read spherically from any direction through most materials, and including most importantly those materials comprising implants for the human body. The transponder may be directly encoded with up to 64 binary bits of data to provide almost one trillion possible different code combinations. It is anticipated that FDA approval will be forthcoming for its use as part of the invention disclosed and claimed herein.

Figure 2:
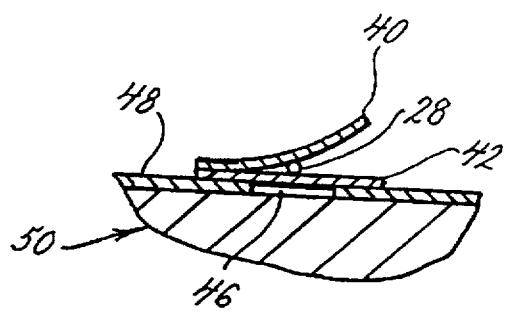
FIG. 2 is a partial cross-sectional view of the transponder as laminated between the multiple layers of a seal patch for a breast implant.

A hand held reader 34 is also shown in FIG. 1 and may be a Trovan Model LID500, or other suitable device. Its principle of operation includes emitting a low frequency magnetic field for activating the passive transponder 28. As such, transponder 28 has no power source and instead derives the energy needed for its operation from the magnetic field generated by the reader 34. This permits the transponder 28 to have a virtually unlimited life span. The hand held reader 34 is shown connected to a decoder controller 36 which accesses a data bank 38 in response to the detected code contained within transponder 28 to thereby access such data which has been stored corresponding to transponder 28. Alternately, as mentioned above, the hand held reader 34 may be used to access the code contained within transponder 28 and then other means used to access a data bank for the retrieval of the desired information. Such means might include the use of a telephone and modem to access a registry contained in a geographically centrally located site. As shown in FIG. 2, the transponder 28 may be laminated between adjacent layers 40, 42 of the seal patch 44 which is commonly used to seal the mandrel opening 46 in a shell 48 of a breast implant 50. For other implants, convenient mounting locations may be readily determined with due consideration given to avoiding discomfort to the patient as well as optimizing readability of the transponder with the hand held reader.

Figure 3:
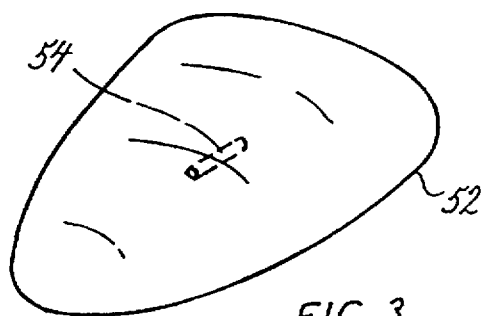
FIG. 3 is a perspective view of a pectoralis muscle implant with a passive transponder mounted therein.

As shown in FIG. 3, a pectoralis muscle implant 52 may conveniently have a passive transponder 54 contained therein. The passive transponder 54 may be molded in place, or a hole or inlay drilled for placement of the implant, after which the implant surface may then be refinished.

As shown in FIGS. 4 and 5, a soft chin implant 56 or a hard chin implant 58 may also have a passive transponder 60, 62 mounted therein. As shown in FIG. 6, a nipple implant 64 has a passive transponder 66 mounted internally. In all of these transplants, the mounting of the passive transponder is achieved to provide minimal discomfort or sensation to the patient, as well as to avoid interference with the cosmetic appearance of the implant. As shown in FIG. 7, an otoplasty implant 68 may have a passive transponder 70 mounted therein. As shown in FIG. 8, a penile implant 72 may have a passive transponder 74 mounted therein.

As shown in FIG. 9, a pace maker 76 may also have a passive transponder 78 mounted either on its surface or below the protective metal casing thereof. The inventors have found that reading of the passive transponder by the hand held reader may be achieved even when the transponder is obscured by metallic surfaces. As shown in FIG. 10, a heart valve 80 may have a passive transponder 82 mounted to its edge in order to avoid interference with the operability thereof, or fixation thereof.

Figure 11:
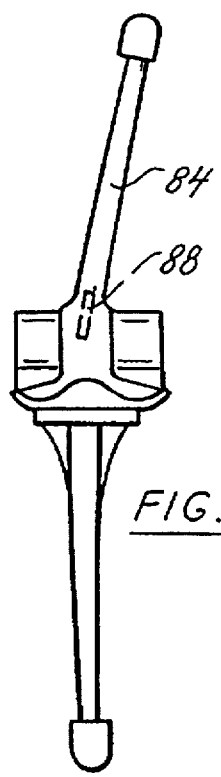
FIG. 11 is a perspective view of a total knee joint prosthesis with a-passive transponder mounted thereon.
Figure 12:
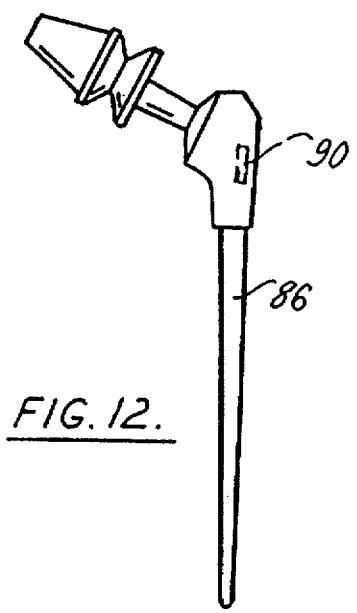
FIG. 12 is a perspective view of a shoulder arthroplasty system with a passive transponder mounted therein.

As shown in FIGS. 11 and 12, a total knee joint prosthesis 84 or a shoulder prosthesis 86, either one of which includes a majority of parts made from titanium or the like, may also conveniently carry a passive transponder 88, 90.

Figure 13:
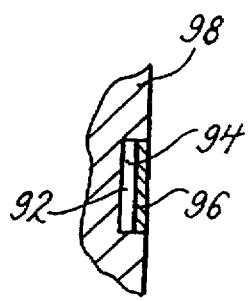
FIG. 13 is a partial cross-sectional view of a passive transponder inlaid into and below the surface of an implant.

As shown in FIG. 13, the passive transponder 92 may be placed within a trough 94 or the like and covered with a sealant 96 so that the surface of the transponder 98 is uninterrupted and smooth as is desirable in many transponders.

Figure 15:
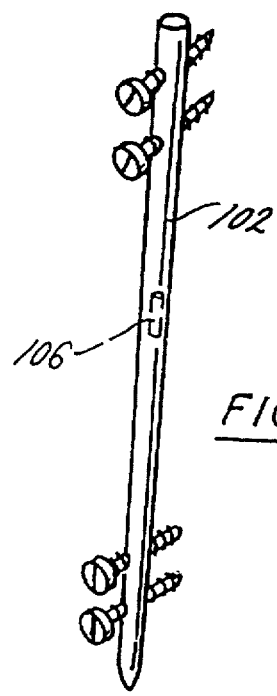
FIG. 15 is a perspective view of an orthopedic nailing system with a passive transponder mounted therein.
Figure 14:
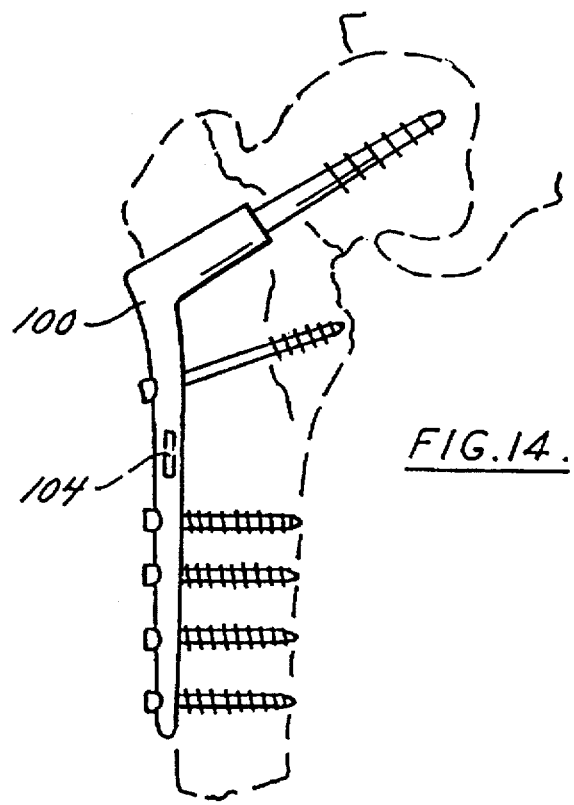
FIG. 14 is a perspective view of a femoral fixation system implanted in a femur with a passive transponder mounted thereto.
Figure 16:
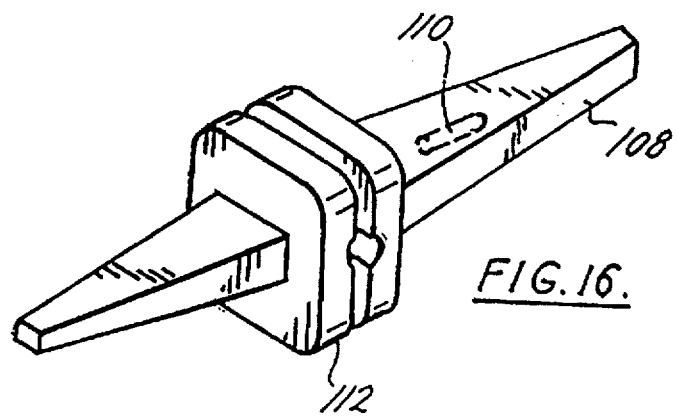
FIG. 16 is a perspective view of a finger joint prosthesis with a passive transponder mounted therein.
Figure 17:
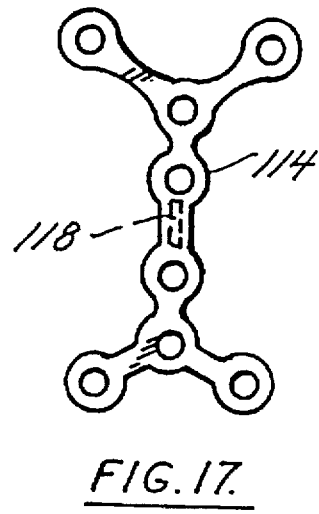
FIG. 17 is a perspective view of a crantomaxillofacial plating system with a passive transponder mounted therein.
Figure 18:
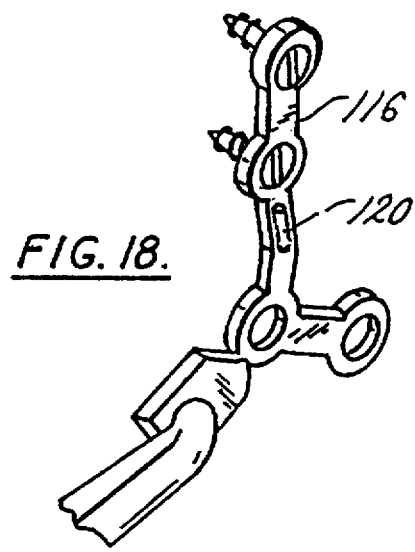
FIG. 18 is a perspective view of still another plating system with a passive transponder mounted therein.
Figure 19:
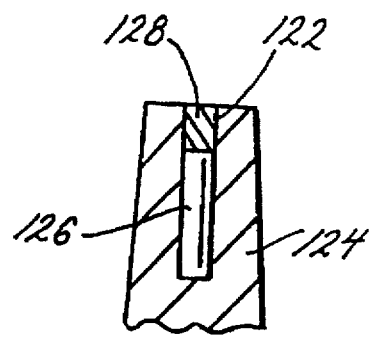
FIG. 19 is a partial cross-sectional view of a typical implant with a passive transponder mounted within a cored hole drilled therein.

As shown in FIGS. 14 and 15, a femoral fixation implant 100, or an orthopedic nailing system 102 may conveniently have a passive transponder 104, 106 inlaid therein. As shown in FIG. 16, a finger joint prosthesis 108 may also have a passive transponder 110 located in a position which does not interfere with the moveable joint portion 112 of the prosthesis 108. As shown in FIGS. 17 and 18, a craniom-axillofacial plating system 114 or any other plating system 116 may also conveniently include a passive transponder 118, 120. As an alternative to the inlay mounting shown in FIG. 13, a hole 122 may be drilled in any convenient location of an implant 124 and the passive transponder 126 inserted therein and sealed in place by sealer 128, with the outer surface of sealer 128 being finished to provide a smooth surface on implant 124.

Figure 20:
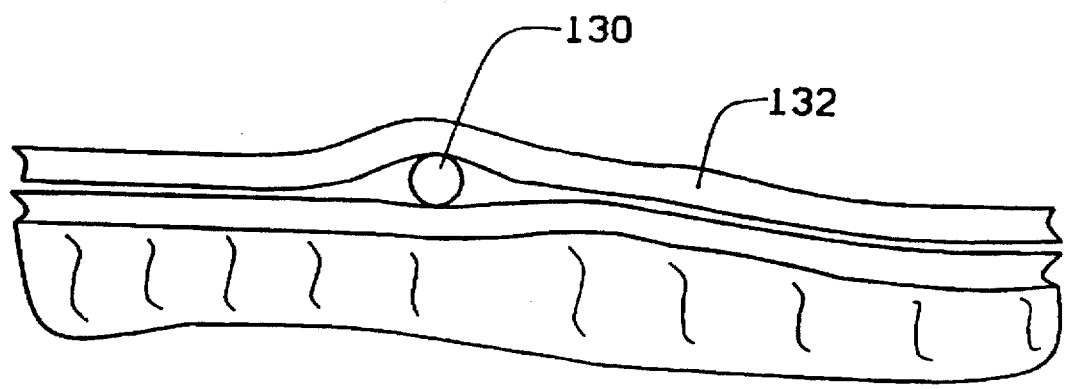
FIG. 20 is a partial cross-sectional view of a transponder implanted subcutaneously.
Figure 21:
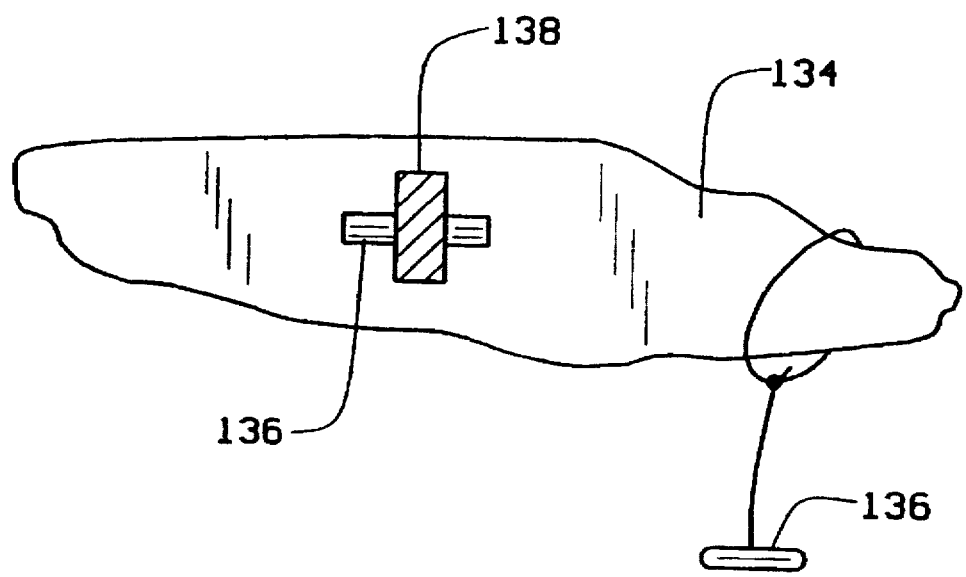
FIG. 21 is a perspective view of a living organ with a transponder affixed thereto.

As shown in FIG. 20, a passive transponder 130 may be implanted subcutaneously beneath an upper layer of skin 132. This upper layer of skin 132 may be grafted onto the patient at the time of implantation, such as would be possible for a burn victim, reconstructive surgery of the breast, etc. Alternately, the transponder 130 may be implanted subcutaneously when it is not feasible or desirable to directly associate the transponder 130 with the living tissue or organ being implanted. An example of such a situation would be a cornea transplant patient. As shown in FIG. 21, living tissue 134, which may be an organ, may have a transponder 136 affixed thereto with any convenient means such as surgical tape 138. In this situation, the transponder 136 need not be separately handled and may instead be surgically implanted at the time that the living tissue 134 is implanted. It should be noted that living tissue implants are not limited to human tissue. AS is well known in the medical community, other mammalian tissue has been implanted and there is ongoing research with respect to genetically engineering animals to serve as donors for human organs such as kidney, lungs, and hearts. Still other examples of living tissue implants include artificial organs composed partially of living cells and partially of synthetic materials. Examples of these include an artificial pancreas and liver which combines cell tissue with man made materials for long term implantable devices. As mentioned above, the transponder may be secured directly to the living tissue by surgical tape or the like. Other acceptable methodologies for associating the transponder with the living tissue including utilizing a non-absorbable "string and basket" tether or by locating the transponder according to an "adjacent site" standard. This adjacent site may be in very close proximity to the implant or in a standardized location that may be device specific.

As disclosed herein, a wide variety of implants made of all sorts of material and including living tissue may conveniently include a passive transponder which may be implanted, and then read by the hand held reader. This compatibility and ease of operation permits the use of a passive transponder with virtually any implant. The inventors have disclosed herein a representative sample of such implants. However, the scope of the present invention is broad enough to encompass any implant presently known to the inventors herein.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for rendering identifiable a transplant member comprised at least in part of living tissue, said method comprising the steps of:

encoding a transponder with information concerning said transplant member, and contemporaneously transplanting said transplant member and implanting said transponder in a human, said transponder being encoded in a manner so that such information may be readily retrieved with a procedure which is noninvasive to the human.

2. The method of claim 1 further comprising the step of physically securing said transponder to said transplant member so that said transplant member and transponder are implanted together and in physical proximity with each other.

3. The method of claim 1 wherein the step of physically securing includes affixing the transponder to the transplant member.

4. The method of claim 1 further comprising mounting the transponder within the profile of the transplant member.

5. The method of claim 1 wherein the transplant member is totally comprised of living tissue.

6. The method of claim 1 wherein the step of encoding said transponder comprises the step of encoding said transponder in a manner to enable the transponder to be read electromagnetically with the implant.

7. A method for rendering identifiable a transplant member in a human, the method comprising the steps of:

encoding a transponder with information concerning a transplant member comprised at least in part of living tissue, and transplanting said transplant member and implanting said transponder in a human, said transponder being encoded in a manner so that such information may be readily retrieved with a procedure which is noninvasive to the human.

8. The method of claim 7 wherein the step of transplanting said transplant member and implanting said transponder in a human comprises contemporaneously transplanting said transplant member and implanting said transponder in a human.

9. The method of claim 7 further comprising the step of mounting the transponder within the profile of the transplant member.

10. The method of claim 7 wherein the step encoding a transponder with information concerning a transplant member comprised at least in part of living tissue comprises the step of encoding the transponder with information concerning a transplant member totally comprised of living tissue.

11. The method of claim 7 wherein said transponder is encoded in a manner to be read electromagnetically.

* * * * *